(12) United States Patent
Cobble, Jr.

(10) Patent No.: US 10,076,551 B2
(45) Date of Patent: Sep. 18, 2018

(54) METHOD FOR TREATING INTERSTITIAL LUNG DISEASE

(71) Applicant: Fredrick Cobble, Jr., Las Vegas, NV (US)

(72) Inventor: Fredrick Cobble, Jr., Las Vegas, NV (US)

(*) Notice: Subject to any disclaimer, the term of this patent is extended or adjusted under 35 U.S.C. 154(b) by 0 days.

(21) Appl. No.: 15/809,352

(22) Filed: Nov. 10, 2017

(65) Prior Publication Data

US 2018/0133277 A1    May 17, 2018

Related U.S. Application Data

(60) Provisional application No. 62/421,846, filed on Nov. 14, 2016.

(51) Int. Cl.
| | | |
|---|---|---|
| A61K 36/00 | (2006.01) | |
| A61K 36/886 | (2006.01) | |
| A61K 9/00 | (2006.01) | |
| A61K 31/19 | (2006.01) | |
| A61K 36/61 | (2006.01) | |

(52) U.S. Cl.
CPC ............ *A61K 36/886* (2013.01); *A61K 9/007* (2013.01); *A61K 31/19* (2013.01); *A61K 36/61* (2013.01)

(58) Field of Classification Search
CPC .................................................. A61K 36/00
See application file for complete search history.

(56) References Cited

U.S. PATENT DOCUMENTS

| | | | |
|---|---|---|---|
| 2010/0322976 A1* | 12/2010 | Sharma | A61K 36/33 424/278.1 |
| 2011/0112049 A1 | 5/2011 | Brown | |
| 2013/0311055 A1 | 11/2013 | Whitney et al. | |
| 2014/0100214 A1 | 4/2014 | Castro et al. | |
| 2014/0349375 A1 | 11/2014 | Benjamin et al. | |
| 2015/0034077 A1 | 2/2015 | Kraft et al. | |
| 2015/0246932 A1 | 9/2015 | Castro et al. | |
| 2016/0058772 A1 | 3/2016 | Baker | |
| 2016/0158179 A1 | 6/2016 | Baker, Jr. et al. | |
| 2016/0184313 A1 | 6/2016 | Brew et al. | |

FOREIGN PATENT DOCUMENTS

| | | |
|---|---|---|
| CN | 104288235 | 1/2015 |
| WO | 2015038892 | 3/2015 |
| WO | 2015073319 | 5/2015 |
| WO | 2015155738 | 10/2015 |

OTHER PUBLICATIONS

Tea tree oil nanoemulsions for inhalation therapies of bacterial and fungal pneumonia Li, M, et al. Colloids and Surfaces B: Biointerfaces; 141: 408-416 Publication Date: 2016.
Modulatory effects of green tea and aloe vera extracts on experimentally-induced lung fibrosis in rats: histological and immunohistochemical study Salem, MY et al. Journal of Histology & Histopathology; 1: Article 6 Jublication Date: 2014.

* cited by examiner

*Primary Examiner* — Qiuwen Mi
(74) *Attorney, Agent, or Firm* — Weiss & Moy, P.C.; Jeffrey D. Moy

(57) ABSTRACT

A method of treating an interstitial lung disease comprises providing tea tree oil in a range of approximately 20%-60% by volume; providing aloe vera in a range of approximately 20% to 60% by volume; providing vinegar in a range of approximately 20% to 60% by volume; combining the tea tree oil, the aloe vera and the vinegar together; placing the combination of the tea tree oil, the aloe vera and the vinegar in a humidifier; and placing a diluent in the humidifier.

15 Claims, 1 Drawing Sheet

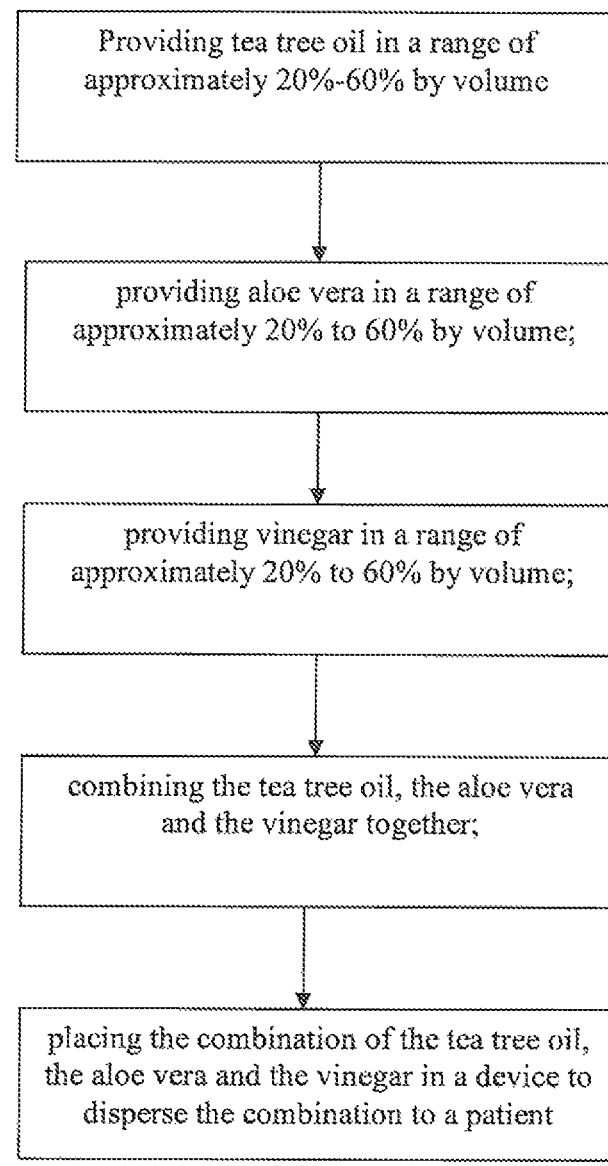

METHOD FOR TREATING INTERSTITIAL LUNG DISEASE

TECHNICAL FIELD

The present application generally relates to scarring of lung tissue, and, more particularly, to a homeopathic treatment for interstitial lung disease which causes scarring of lung tissue which may lead to coughing and the build-up of mucous and which may cause progressive lung stiffness which may eventually affect one's ability to breath an get enough oxygen into the bloodstream and which may lead to death once lung scaring occurs.

BACKGROUND

Interstitial lung disease is a term that may be used to describe many different lung conditions. In general, all interstitial lung diseases affect the interstitium. The interstitum may be defined as a part of the lungs' anatomic structure. More specifically, the interstitum may be a lace-like network of tissue that extends throughout both lungs. The interstitium may provide support to the lungs' microscopic air sacs (i.e., alveoli). Tiny blood vessels may travel through the interstitium, thereby allowing gas exchange between blood and the air in the lungs.

In general, interstitial lung disease describes a large group of disorders, most of which cause progressive scarring of lung tissue between and supporting the air sacs. The scarring associated with interstitial lung disease may cause progressive lung stiffness, which eventually affects the ability to breathe and get enough oxygen into the bloodstream.

Interstitial lung disease seems to occur when an injury to the lungs triggers an abnormal healing response. Ordinarily, the body generates just the right amount of tissue to repair damage. But in interstitial lung disease, the repair process goes awry and the tissue around the air sacs (alveoli) becomes scarred and thickened. Interstitial lung disease can be caused by long-term exposure to different toxins and pollutants within the air that one may breathe. For example, long-term exposure to silica dust, asbestos fibers, grain dust may cause interstitial lung disease. Some types of autoimmune diseases, such as rheumatoid arthritis, also can cause interstitial lung disease. In some cases, however, the causes remain unknown.

Treatments for interstitial lung disease may vary according to the type of interstitial lung disease and its cause. In general, medication such as antibiotics, corticosteroids and as well other medications may be used to treat various types of interstitial lung diseases. Other treatments may include the use of an oxygen breathing machine and/or portable oxygen tank and n severe cases, lung transplant. Unfortunately, most of the above treatments for interstitial lung diseases are expensive. Unfortunately, once lung scarring occurs, it's generally irreversible. Medications may slow the damage of interstitial lung disease, but many people never regain full use of their lungs.

Therefore, it would be desirable to provide a homeopathic treatment and method that overcome the above problems.

SUMMARY

In accordance with one embodiment, a treatment for interstitial lung disease is disclosed. The treatment comprises tea tree oil in a range of approximately 20%-60% by volume; aloe vera in a range of approximately 20% to 60% by volume; and vinegar in a range of approximately 20% to 60% by volume.

In accordance with one embodiment, a method of treating an interstitial lung disease is, disclosed. The method comprising: providing tea tree oil in a range of approximately 20%-60% by volume; providing alo vera in a grange of approximately 20% to 60% by volume; providing vinegar in a range of approximately 20% to 60% by volume; combining the tea tree oil, aloe vera and vinegar together; placing the combination of the tea tree oil, aloe vera and, vinegar in a humidifier; and placing a diluent in the humidifier.

In accordance with one embodiment, a method of treating an interstitial lung disease is disclosed. The method comprising: providing tea tree oil in a range of approximately 1 to 3 teaspoons; providing aloe vera in a range of approximately 1 to 3 teaspoons; providing vinegar in a range of approximately 1 to 3 teaspoons; combining the tea tree oil, the aloe vera and the vinegar together; and placing the combination of the tea tree oil, the aloe vera and the vinegar in a device to disperse the combination to a patient.

BRIEF DESCRIPTION OF THE DRAWINGS

The present application is further detailed with respect to the following drawings. These figures are not intended to limit the scope of the present application but rather illustrate certain attributes thereof. The same reference numbers will be used throughout the drawings to refer to the same or like parts.

FIG. 1 is a flowchart showing a method of treating an interstitial lung disease in accordance with, an embodiment of the present invention.

DESCRIPTION OF THE APPLICATION

The description set forth below in connection with the appended drawings is intended as a description of presently preferred embodiments of the disclosure and is not intended to represent the only forms in which the present disclosure may be constructed and/or utilized. The description sets forth the functions and the sequence of steps for constructing and operating the disclosure in connection with the illustrated embodiments. It is to be understood, however, that the same or equivalent functions and sequences may be accomplished by different embodiments that are also intended to be encompassed within the spirit and scope of this disclosure.

A homeopathic treatment for interstitial lung disease is disclosed. The homeopathic substance may be used with a humidifier and/or oxygen machine to aid a user in breathing in an easier manner.

The homeopathic substance may contain tea tree oil. Tea tree oil (TTO), or melaleuca oil, is an essential oil with a fresh camphoraceous odor and a color that ranges from pale yellow to nearly colorless and clear. It is generally taken from the leaves of the Melaleuca alternifolia.

Tea tree oil may often be used externally as a remedy for a number of conditions including acne, athlete's foot, nail fungus, wounds, and infections; or for lice, oral candidiasis (thrush), cold sores, dandruff, and skin lesions. However, a 2004 NCCIH-funded review examined the ability of tea tree oil to kill bacteria and found that in vitro (in a test tube) studies may provide some preliminary evidence for the use of tea tree, oil as an adjunctive (additional) treatment for wounds involving difficult-to-treat bacterial infections such as methicillin-resistant *Staphylococcus aureus* (MRSA).

The homeopathic substance may contain 20%-60% by volume of tea tree oil. In accordance with one embodiment, the tea tree oil is pharmaceutical grade tea tree oil.

The homeopathic substance may contain aloe vera. In accordance with one embodiment, the homeopathic substance may contain aloe vera juice. Aloe vera juice is generally the juice, and in some cases, the leaf pulp extracted from the aloe vera plant.

Aloe vera contains anti-bacterial, anti-viral and anti-fungal properties that aid the immune system to cleanse the body of toxins and invading pathogens. Additionally, aloe vera helps to balance the immune system to reduce the effects of seasonal allergies, rheumatoid arthritis and other inflammatory immune disorders.

The homeopathic substance may contain 20%-60% by volume of aloe vera juice. In accordance with one embodiment, the homeopathic substance may contain 20%-60% by volume of filtered aloe vera juice, wherein the aloe vera juice is organic. Preferably, the purer the aloe vera juice the better. In accordance with one embodiment, the aloe vera juice is 99% organic.

The homeopathic substance may contain vinegar. Vinegar is a liquid which may contain about 5-20% acetic acid ($CH_3COOH$), water, and other trace chemicals, which may include flavorings. Vinegar has been shown to have and used as an antimicrobial agent. Vinegar has been used for centuries as a health tonic with a variety of medical uses. It has been used as a treatment for allergies, flu, sore throat, acid reflux, gout and other ailments.

The homeopathic substance may contain 20%-60% by volume of vinegar. In accordance with one embodiment, the homeopathic substance may contain 20%-60% by volume of white vinegar apple vinegar.

In accordance with one embodiment, the homeopathic substance may contain 1-3 tablespoons of pharmaceutical grade tea tree oil, 1-3 tablespoons of filter aloe vera juice which may be 99% organic and 1-3 tablespoons of white or apple vinegar.

In accordance with another embodiment, the homeopathic substance may be comprised of a combination of sunflower oil and aloe vera. Sunflower oil is the non-volatile oil compressed from the seeds of sunflower. The homeopathic substance may be comprised of 14-33% by volume of sunflower oil and 67%-86% by volume of aloe vera. As in the previous embodiment, the aloe vera is an aloe vera juice. The aloe vera juice may be a filtered aloe vera juice, wherein the aloe vera juice is organic. Preferably, the purer the aloe vera juice the better. In accordance with one embodiment, the aloe vera juice is 99% organic.

The above homeopathic substances may be placed in a humidifier. In the embodiment where the homeopathic substance may contain 1-3 tablespoons of pharmaceutical grade tea tree oil, 1-3 tablespoons of filter aloe vera juice which may be 99% organic and 1-3 tablespoons of white or apple vinegar, the amount placed in the humidifier may be 3-9 tablespoons. When placed in a humidifier, the homeopathic substance may be combined with a diluent. For example, water may be placed in the humidifier. In accordance with one embodiment, room temperature water may be placed in the humidifier. The amount of water added should be sufficient to disseminate the homeopathic substance into the air. For example, in the above embodiment, six to eight ounces of water may be placed in the humidifier to disseminate the homeopathic substance into the air. The person suffering from the interstitial lung disease may then breathe in the steam mixed with the homeopathic substance. The person may do this while sleeping, thus breathing the substance for 6-10 hours.

The homeopathic substance may be used with an oxygen machine. The oxygen machine may have an injection port for adding the homeopathic substance. This may allow the user to breath in the homeopathic substance.

While embodiments of the disclosure have been described in terms of various specific embodiments, those skilled in the art will recognize that the embodiments of the disclosure may be practiced with modifications within the spirit and scope of the claims

The invention claimed is:

1. A method of treating an interstitial lung disease comprising administering to a patient in need thereof an effective amount of a composition through inhalation, the method comprising:
   providing tea tree oil in a range of approximately 20%-60% by volume;
   providing aloe vera in a range of approximately 20% to 60% by volume;
   providing vinegar in a range of approximately 20% to 60% by volume;
   combining the tea tree oil, the aloe vera and the vinegar together;
   placing the combination of the tea tree oil, the aloe vera and the vinegar in a humidifier;
   placing a diluent in the humidifier;
   activating the humidifier to generate a steam, wherein the steam is a combination of the tea tree oil, the aloe vera, the vinegar and the diluent; and
   inhalation of the steam by the patient.

2. The method of claim 1, comprising breathing the steam for 6-10 hours by the patient.

3. The method of claim 1, wherein the tea tree oil is pharmaceutical grade tea tree oil.

4. The method of claim 1, wherein the aloe vera is aloe vera juice.

5. The method of claim 1, wherein the aloe vera is organic aloe vera juice.

6. The method of claim 1, wherein the vinegar is one of white vinegar or apple vinegar.

7. The method of claim 1, wherein the diluent is water.

8. The method of claim 7, comprising adding 6 to 8 ounces of the water to the humidifier.

9. A method of treating an interstitial lung disease comprising administering to a patient in need thereof an effective amount of a composition through inhalation, the method comprising the steps of:
   providing tea tree oil in a range of approximately 1 to 3 teaspoons;
   providing aloe vera in a range of approximately 1 to 3 teaspoons;
   providing vinegar in a range of approximately 1 to 3 teaspoons;
   combining the tea tree oil, the aloe vera and the vinegar together;
   placing the combination of the tea tree oil, the aloe vera and the vinegar in a device to disperse the combination to a patient; and
   inhaling the combination of the tea tree oil, the aloe vera and the vinegar dispersed by the device by the patient.

10. The method of claim 9, wherein placing the combination of the tea tree oil, the aloe vera and the vinegar in a device to disperse the combination to a patient comprises:
    placing the combination of the tea tree oil, the aloe vera and the vinegar in a humidifier;

placing a diluent in the humidifier; and breathing a steam emanating from the humidifier, wherein the steam is a combination of the tea tree oil, the aloe vera, the vinegar and the diluent.

11. The method of claim 10, comprising breathing the steam for 6-10 hours.

12. The method of claim 9, wherein placing the combination of the tea tree oil, the aloe vera and the vinegar in a device to disperse the combination to a patient comprises placing the combination in an oxygen breathing device.

13. The method of claim 9, wherein the aloe vera is organic aloe vera juice.

14. The method of claim 9, comprising adding 6 to 8 ounces of the water to the humidifier as the diluent.

15. A method of treating an interstitial lung disease comprising administering to a patient in need thereof an effective amount of a composition through inhalation, the method comprising:

providing tea tree oil in a range of approximately 20%-60% by volume;

providing aloe vera in a range of approximately 20% to 60% by volume;

providing vinegar in a range of approximately 20% to 60% by volume;

combining the tea tree oil, the aloe vera and the vinegar together;

placing the combination of the tea tree oil, the aloe vera and the vinegar in a humidifier;

adding 6 to 8 ounces of water to the humidifier;

activating the humidifier to generate a steam, wherein the steam is a combination of the tea tree oil, the aloe vera, the vinegar and the water; and inhalation of the steam by the patient for 6-10 hours.

* * * * *